(12) United States Patent
Fleischman et al.

(10) Patent No.: US 7,284,442 B2
(45) Date of Patent: Oct. 23, 2007

(54) METHOD AND APPARATUS FOR IN VIVO SENSING

(75) Inventors: Aaron J. Fleischman, University Heights, OH (US); James R. Talman, Crofton, MD (US); Shuvo Roy, Shaker Heights, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 11/441,855

(22) Filed: May 26, 2006

(65) Prior Publication Data

US 2007/0049845 A1    Mar. 1, 2007

Related U.S. Application Data

(60) Provisional application No. 60/685,729, filed on May 27, 2005.

(51) Int. Cl.
*A61B 5/05*    (2006.01)
(52) U.S. Cl. .......................................... 73/753; 600/345
(58) Field of Classification Search .................. 73/700, 73/753, 754; 600/345
See application file for complete search history.

(56) References Cited

U.S. PATENT DOCUMENTS

| | | | |
|---|---|---|---|
| 4,114,601 A | 9/1978 | Abels | |
| 5,626,630 A | 5/1997 | Markowitz et al. | |
| 5,967,986 A | 10/1999 | Cimochowski et al. | |
| 6,682,480 B1 | 1/2004 | Habib et al. | |
| 2004/0133131 A1* | 7/2004 | Kuhn et al. | 600/593 |
| 2005/0165317 A1 | 7/2005 | Turner et al. | |
| 2006/0074479 A1* | 4/2006 | Bailey et al. | 623/1.13 |

FOREIGN PATENT DOCUMENTS

| WO | WO 2000/013585 A2 | 3/2000 |
|---|---|---|
| WO | WO 2005/027998 A2 | 3/2005 |

\* cited by examiner

*Primary Examiner*—Andre J Allen
(74) *Attorney, Agent, or Firm*—Tarolli, Sundheim, Covell & Tummino LLP

(57) ABSTRACT

Systems and methods for in vivo sensing are provided. An excitation signal is produced, having a first frequency component and a second frequency component. The first frequency component is swept through a plurality of excitation frequencies within a frequency range of interest. A response signal is received from an in vivo sensor. The response signal includes a mix component having a frequency equal to one of a sum of a first excitation frequency associated with the first frequency component and a second excitation frequency associated with the second frequency component and a difference between the first and second excitation frequencies. The mix component is evaluated to determine a resonant frequency of the in vivo sensor.

20 Claims, 5 Drawing Sheets

METHOD AND APPARATUS FOR IN VIVO SENSING

RELATED APPLICATION

This application claims priority from U.S. provisional patent application Ser. No. 60/685,729, filed on May 27, 2005, the subject matter of which is incorporated herein by reference.

FIELD OF THE INVENTION

The present invention relates to a method and apparatus for in vivo sensing and, in particular, is directed to a method and apparatus for determining a characteristic of an in vivo sensor.

BACKGROUND OF THE INVENTION

Information regarding the conditions inside a body cavity in a patient, such as a human, can be very helpful to a physician treating the patient. For example, it is desirable to monitor intercranial pressure to look for problems such as hemorrhaging and tumors. As another example, it is also desirable to monitor the pressure inside various blood vessels in the human body to help determine if a problem, such as stenosis or an aneurysm, exists. Due to the difficulties of providing power to a device within the body, passive sensors are often used for in vivo sensing. Passive sensors can be fabricated to detect pressure, temperature, pH, etc, by causing one element of the resonant circuit to change in response to the quantity being detected. This changes the resonant frequency of the device, and this change in resonant frequency can be detected externally using a radiofrequency (RF) probe.

Microelectromechanical systems, or MEMS, are a class of miniature electromechanical components and systems that are fabricated using techniques originally developed for fabricating microelectronics. MEMS devices, such as pressure sensors and strain gauges, manufactured using microfabrication and micromachining techniques can exhibit superior performance compared to their conventionally built counterparts, and are resistant to failure due to fatigue, corrosion, etc. Further, due to their extremely small size, MEMS devices can be utilized to perform functions in unique applications, such as the human body, that were not previously feasible using conventional devices.

Recently there has been considerable interest in exploiting microelectromechanical system (MEMS) technology to simplify the fabrication and reduce the cost of in vivo sensors. In many implementations, the RF probe used to detect the resonant frequency of a passive sensor uses a "grid-dip oscillator" approach. An oscillating RF current flows through an RF coil, inducing currents in the inductance coil of a nearby sensor. The loading effect of the sensor on the RF transmit coil results in a decrease or "dip" in the phase response of the transmitter current and the frequency at which this occurs is used to deduce the value of the quantity being measured. This method benefits from the simplicity of a single RF coil, but frequency measurements are complicated by difficulties associated with separating the small receive signal from the large oscillation signal.

SUMMARY OF THE INVENTION

In accordance with one aspect of the present invention, a method for in vivo sensing is provided. An excitation signal is produced, having a first frequency component and a second frequency component. The first frequency component is swept through a plurality of excitation frequencies within a frequency range of interest. A response signal is received from an in vivo sensor. The response signal includes a mix component having a frequency equal to one of a sum of a first excitation frequency associated with the first frequency component and a second excitation frequency associated with the second frequency component and a difference between the first and second excitation frequencies. The mix component is evaluated to determine a resonant frequency of the in vivo sensor.

In accordance with another aspect of the invention, a computer program product, encoded on a computer readable medium and operative in a data processing system, for controlling an RF probe is provided. A frequency selector selects a first excitation frequency and a second excitation frequency for the probe. An amplitude detector determines an associated power of a mix component of a response signal from an in vivo sensor for each of a plurality of selected values for the first excitation frequency to record a frequency response for the signal. The mix component has an associated frequency equal to one of a sum of the first and second excitation frequencies and a difference between the first and second excitation frequencies. A response analyzer evaluates the recorded frequency response to determine a resonant frequency of the in vivo sensor.

In accordance with another aspect of the present invention, an RF probe assembly is provided for determining a resonant frequency of an in vivo sensor having an associated nonlinear element. A transmit element provides an excitation signal for the probe. The excitation signal includes a first frequency component, having a first associated frequency, and a second frequency component, having a second associated frequency. A response element receives a response signal from the in vivo sensor. The response signal includes a mix component having a frequency equal to one of a sum of the first and second frequencies and a difference between the first and second frequencies. A system control evaluates the mix component to determine the resonant frequency of an associated in vivo sensor.

BRIEF DESCRIPTION OF THE DRAWINGS

The foregoing and other features of the present invention will become apparent to those skilled in the art to which the present invention relates upon reading the following description with reference to the accompanying drawings, in which.

DESCRIPTION OF EMBODIMENTS

The present invention relates to an apparatus and method for in vivo measurement of one or more characteristics of interest and, in particular, is directed to an apparatus and method for interrogating an in vivo sensor to determine a characteristic. Potential biomedical applications for the present invention include blood flow and pressure sensors in the vicinity of stents, intraocular pressure sensing for detection of glaucoma, pressure or strain sensors for assessing the progress of spinal fusion procedures, and pressure sensors for monitoring a patient during treatment of hydrocephalus and abdominal aortic aneurysms. It should be understood that this list of potential applications is exemplary in nature and by no means exhaustive.

Figure 1:
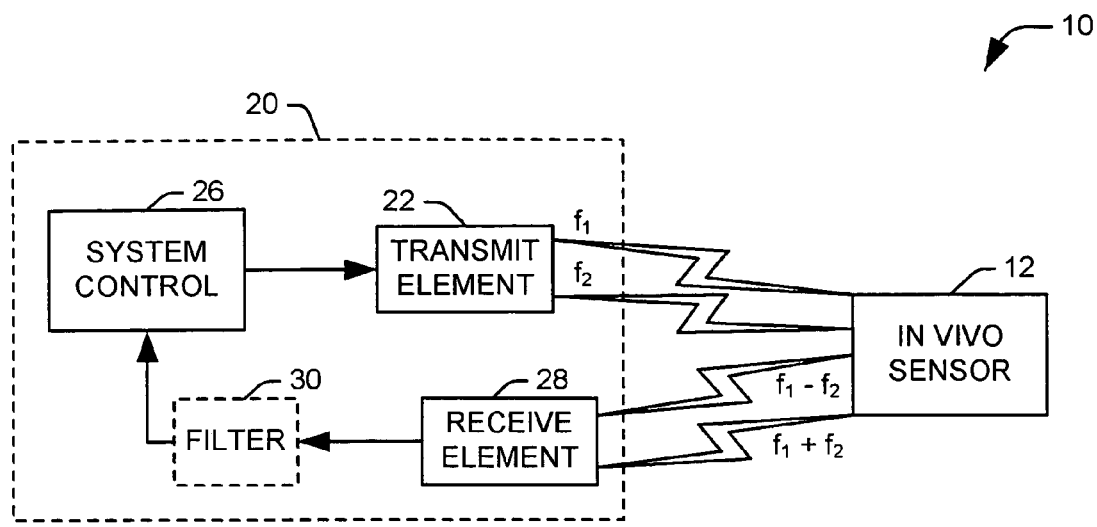
FIG. 1 illustrates a system for determining a characteristic within a living body in accordance with an aspect of the present invention.

As representative of the present invention, FIG. 1 illustrates a system 10 for determining a characteristic within a living body via an in vivo sensor 12 having an associated nonlinear element. For example, the in vivo sensor 12 can comprise a tank circuit sensor having an impedance, capacitance, or quality factor (Q) dependent on an internal characteristic of the body in which it is implanted, such as pressure. The tank circuit sensor can include a nonlinear element, such as a Schottky diode, to adjust the frequency response of the tank circuit. The system includes an apparatus in the form of an RF probe assembly 20 that excites the in vivo sensor 12 and detects a response signal from the sensor. This response signal is analyzed at the probe to determine an associated characteristic of the in vivo sensor 12, and thus, a characteristic of the living body.

The nonlinear element associated with the in vivo sensor 12 causes the sensor to react differently than a standard tank circuit at and around a resonant frequency of the circuit. For example, a different response can be expected when the sensor is excited using either two frequencies or a single frequency. In the former case, presence of the nonlinear component causes a mixing effect, resulting in a response signal having component frequencies equal to the sum and difference of the two input frequencies. In contrast, when a single frequency is used to excite the transmission line, the nonlinear circuit resonates at twice (harmonic) the input frequency.

In accordance with an aspect of the present invention, the RF probe assembly 20 includes a transmit element 22 that provides an excitation signal to the in vivo sensor 12. The excitation signal includes at least first and second frequency components, having respective associated frequencies of $f_1$ and $f_2$, respectively, as selected by a system control 26. For example, the excitation signal can comprise a magnetic field or electromagnetic radiation. The transmit element can comprise one or more transmit coils that are operative to provide the first and second frequency components. The excitation signal induces a response signal at the in vivo sensor 12. In accordance with an aspect of the present invention, the in vivo sensor is configured to respond to the excitation signal with a response signal having a frequency component different in frequency from the frequencies associated with the excitation signal. Specifically, the in vivo sensor 12 acts as a mixer, such that the response signal contains sum and difference mix components having respective frequencies, $f_1+f_2$ and $f_1-f_2$.

The power of the response signal will reach a maximum when one of the frequencies associated with the excitation signal equals the resonant frequency of the sensor 12. The resonant frequency of the sensor 12 is, in turn, a function of the characteristic impedance or capacitance of the sensor 12. The response signal is then received at a receive element 28, comprising one or more receive coils, and provided to the system control 26 for analysis. To minimize coupling between the elements, the one or more coils comprising receive element 28 can be oriented as to be roughly orthogonal to the one or more coils comprising the transmit element 22. The response signal can be filtered at an optional filter 30 to isolate either the sum frequency, $f_1+f_2$, or the difference frequency, $f_1-f_2$, prior to providing the signal to the system control 26.

It will be appreciated that by inducing a response signal frequency that differs from the associated frequencies of the excitation signal, coupling between the transmit and receive elements 22 and 28 can be sharply reduced by providing frequency separation between the transmit signal and the response signal. In an exemplary implementation, the frequency diversity between the response signal and the excitation signal can exploited to allow the transmit and receive elements 22 and 28 to be implemented on a common set of one or more coils. In an exemplary implementation, the difference frequency produced by the sensor can be utilized at the receive element to avoid the attenuating effects of a body on high frequency signals. It will be appreciated that the difference frequency can be arbitrarily selected by varying the frequencies, $f_1$ and $f_2$, such that these attenuating effects can be substantially reduced relative to a system utilizing a common frequency for the excitation signal and the response signal.

In accordance with an aspect of the present invention, the system control 26 can sweep the frequencies, $f_1$ and $f_2$, of the excitation signal through a frequency range of interest, maintaining a small, fixed difference between the frequencies. Accordingly, the response signal produced by the in vivo sensor 12 will contain a constant frequency difference component throughout the frequency sweep. In accordance with another aspect of the present invention, the frequencies, $f_1$ and $f_2$, can be swept in equivalent increments in different directions, such that the sum, $f_1+f_2$, of the frequencies remains constant. This constant sum or difference frequency can be isolated and evaluated at the system control 28. It will be appreciated that by maintaining the frequency component of interest at a fixed frequency, the frequency component of interest can be more easily and accurately isolated.

As discussed above, the power of the response signal will increase when a frequency of the excitation signal approaches the resonant frequency of the sensor 12. The system control 28 can record the power of the response signal at each pair of excitation frequencies across the frequency range of interest. The resulting frequency response will have a peak near the resonant frequency of the sensor 12 and a reasonably flat response elsewhere, forming a reasonably level noise floor at the remaining frequencies. A quality factor (Q) associated with the sensor can be determined by examining the peak response of the sensor, specifically, by measuring the peak width via an appropriate measure (e.g., peak width at half maximum). Accordingly, the desired characteristic of the sensor can be determined, and a corresponding characteristic of the living body can be calculated from the determined characteristic.

Figure 2:
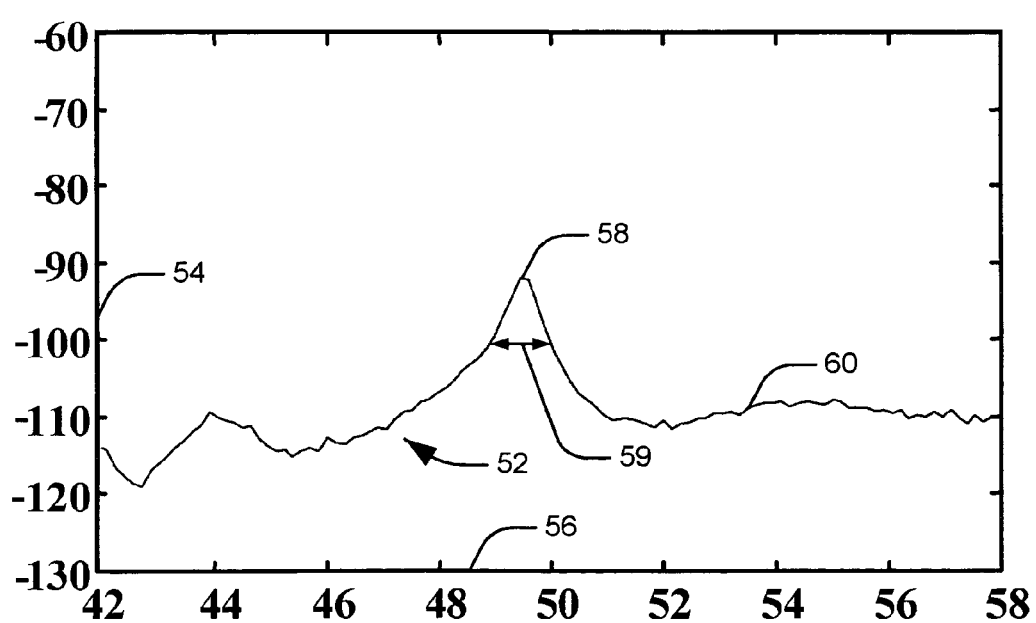
FIG. 2 illustrates a chart of an exemplary frequency response of an in vivo sensor to an excitation signal from an associated probe in accordance with an aspect of the present invention.

FIG. 2 illustrates a chart 50 of an exemplary frequency response 52 of an in vivo sensor to an excitation signal from an associated probe in accordance with an aspect of the present invention. The frequency response 52 is plotted on a vertical axis 54, representing the magnitude, $V_{out}$, of the response in decibels (dB) relative to a reference magnitude, $V_{ref}$, and a horizontal axis 56, representing a first frequency, $f_1$, of the excitation signal in MHz. The frequency response 52 rises to a peak power 58 at a resonant frequency, $f_r$. The peak associated with the resonant frequency has an associated peak width 59 that is a function of a quality factor associated with the in vivo sensor. At all other points, the frequency response remains at or around a noise floor 60 associated with the probe. Accordingly, an analysis of the frequency response 52 for the probe can provide an indication both of a level of noise associated with the probe, the resonant frequency, and an associated quality factor of the in vivo circuit. One or more characteristics of the environment in which the in vivo sensor is implanted can be determined from these qualities according to the design of the in vivo sensor.

Figure 3:
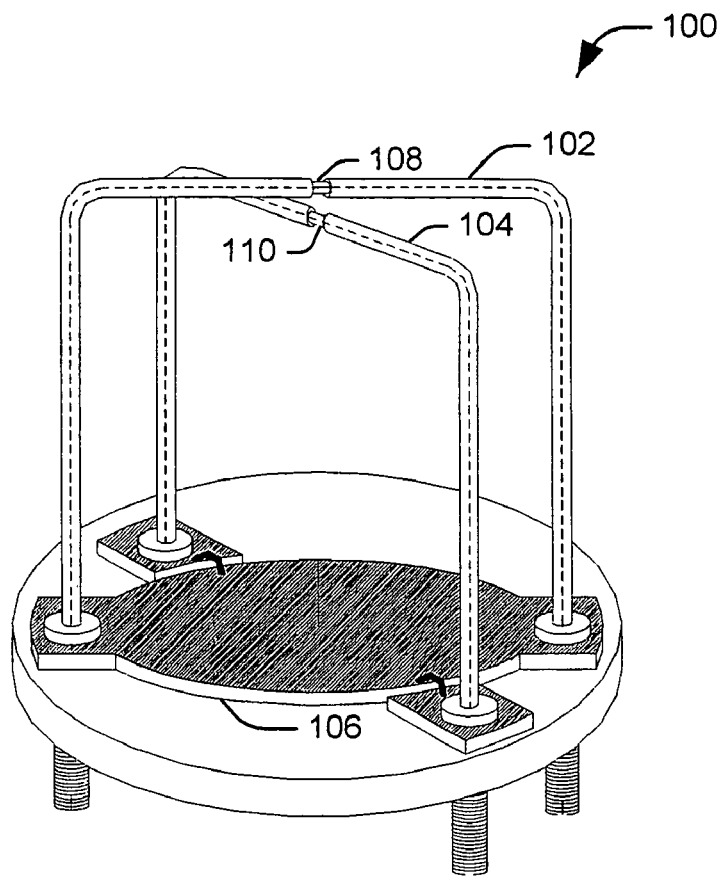
FIG. 3 illustrates an exemplary RF probe that can be utilized in accordance with an aspect of the present invention.

FIG. 3 illustrates an exemplary RF probe 100 that can be utilized in accordance with an aspect of the present invention. The RF probe 100 consists of two orthogonal shielded loops, a transmit loop 102 and a receive loop 104. A swept-frequency transmit signal from a system control is applied to the transmit loop 102, and a response signal received at the receive loop 104 is displayed. Each shielded loop may be modeled, as a practical matter, as a combination of transmission lines. Input and output transmission lines for carrying signals to and from the RF probe 100 are formed between a center conductor of a given loop (e.g., 102) and the inner surface of a conductive shield surrounding the center conductor. Another transmission line is formed between the two outer surfaces of the two halves of the loop 102, and is effectively terminated with a short circuit due to a ground plane 106 at the bottom of the RF probe 100. The outer surfaces of the conductive shields provide a path for the current on the inner surface of the conductive shields to flow around respective gaps 108 and 110 at the top of the loops 102 and 104, thereby forming a closed circuit.

The second transmission line is non-uniform, since the distance between the outer surfaces is not constant. However, it may be modeled accurately for purposes of computing input impedances by an equivalent 2-conductor, parallel-wire transmission line, with short-circuit termination. The thicknesses of the two equivalent conductors are the same as for the probe loops, and the length of the equivalent conductors is equal to the half-perimeter of the shielded loop, as measured on a centerline of the loop, including the ground plane "leg." The spacing between the two equivalent conductors is selected to make the area of the effective transmission line equal to the area of the actual shielded loop.

Figure 4:
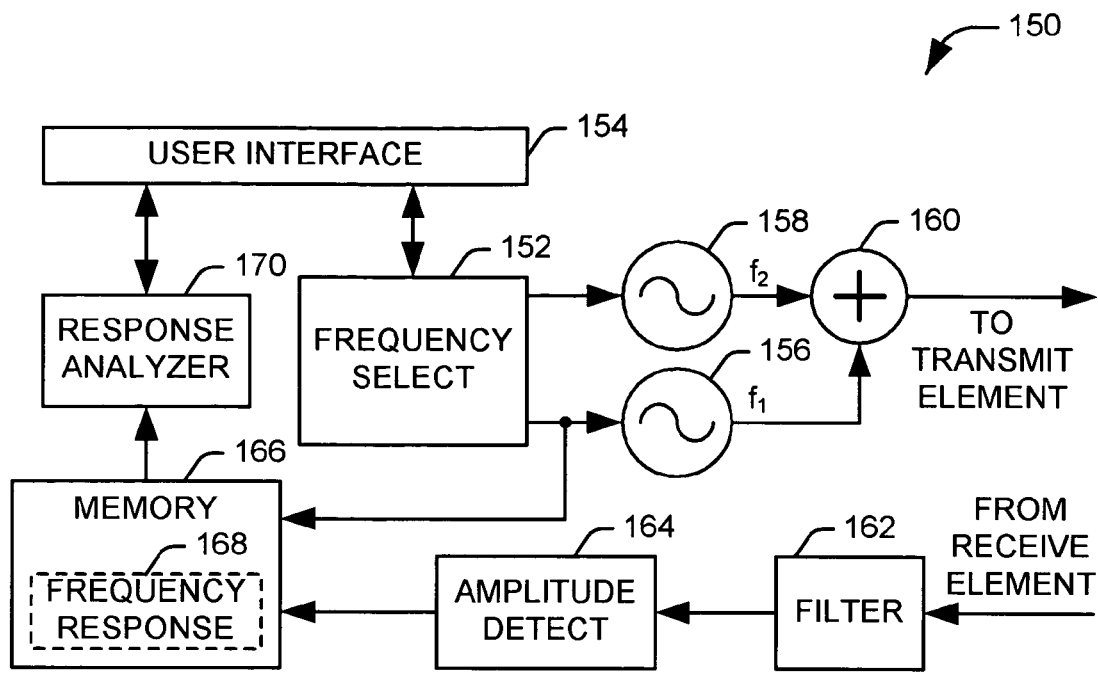
FIG. 4 illustrates an exemplary control module for an RF probe in accordance with an aspect of the present invention.

FIG. 4 illustrates an exemplary control module 150 for an RF probe in accordance with an aspect of the present invention. It will be appreciated that the illustrated control module 150 is configured for use with a single transmit coil and a single receive coil, but one skilled in the art will appreciated that the illustrated control module 150 can be adapted for use with a probe having sets of two or more transmit or receive coils or a single coil or set of coils utilized for both transmitting an excitation signal and receiving a response signal. In an exemplary implementation, all or a portion of the components within the illustrated control module 150 can be implemented as software on a general purpose processor associated with the probe. Individual components within the control module can thus be conceptualized as software modules resident within the processor.

First and second excitation frequencies, $f_1$ and $f_2$, are selected at a frequency selector 152. For example, the frequency selector 152 can select a minimum frequency within a frequency range of interest as the first excitation frequency and advance through the range of interest by a predetermined sweep increment until a maximum frequency associated with the range of interest is achieved. A second excitation frequency, $f_2$, can be determined by adding a fixed offset value to the first excitation frequency, maintained at a constant value, or selected as to maintain a constant sum, $f_1+f_2$. Default values for one or more of the excitation frequencies, a frequency range of interest, a fixed offset value or sum, and a sweep increment can be provided as configuration data within the control module. In an exemplary implementation, the frequency range of interest for a given application, these values can be selected by a user at a user interface 154.

Control data associated with the selected frequencies can be provided to respective first and second oscillators 156 and 158. In some applications, the oscillators 156 and 158 can be implemented digitally, with the output of the digital oscillators being provided to a transmit coil of the probe via a digital-to-analog converter (not shown). In the illustrated example, however, the oscillators 156 and 158 are implemented as digitally controlled oscillators, each operative to produce signals of a desired frequency in response to the control data provided by the frequency selector 152. The outputs of the oscillators 156 and 158 are provided to a signal adder 160. The signal adder 160 sums the signals and provides a combined signal to the transmit coil. It will be appreciated that the various components can be implemented in any of a number of ways. In one implementation, an arbitrary waveform generator can be used to implement, in whole or in part, one or more of the frequency selector 152, the user interface 154, the oscillators 156 and 158, and the signal adder, 160.

Turning to a response path of the control module 150, a response signal from an in vivo sensor is received at a receive coil associated with the RF probe and provided to a filter 162 that isolates a desired sum or difference frequency. The response signal comprises frequency components having associated frequencies equal to the sum and difference of the excitation frequencies. The filter 162 is configured to allow frequencies in the range of one or both of the sum or difference frequency to pass through to an amplitude detect component 164. In accordance with an aspect of the present invention, the difference between two excitation frequencies can be maintained at a fixed offset, such that the difference frequency component within the response signal remains at a fixed difference frequency, $f_1-f_2$. Where the difference frequency is constant, the filter 162 can be implemented as a bandpass filter that works in combination with a lock-in amplifier to isolate and amplify a mix component constant having a constant difference frequency.

The amplitude detect component 164 determines the power of the response signal for each excitation frequency in the frequency range of interest. The determined power and the first excitation frequency can be provided to a system memory 166 and stored as part of a frequency response 168. When complete, the frequency response 168 comprises an associated power for each of a plurality of excitation frequencies within the frequency range of interest. This frequency response 168 can be provided to a response analyzer 170 that determines a frequency associated with a peak power within the frequency response 168. The response analyzer 170 can also calculate the impedance, quality factor, or other desired characteristic of the in vivo sensor. The frequency response 168 and the determined characteristic can be displayed to the user through the user interface 154.

It will be appreciated that the various components can be implemented in any of a number of ways. In one implementation, an arbitrary waveform generator can be used to implement, in whole or in part, one or more of the frequency selector 152, the user interface 154, the oscillators 156 and 158, and the signal adder, 160, and a network analyzer can be utilized to implement, in whole or in part, one or more of the user interface 154, the filter 162, the amplitude detector 164, and the memory 168. Other implementations will be apparent to one skilled in the art in light of the teachings herein.

Figure 5:
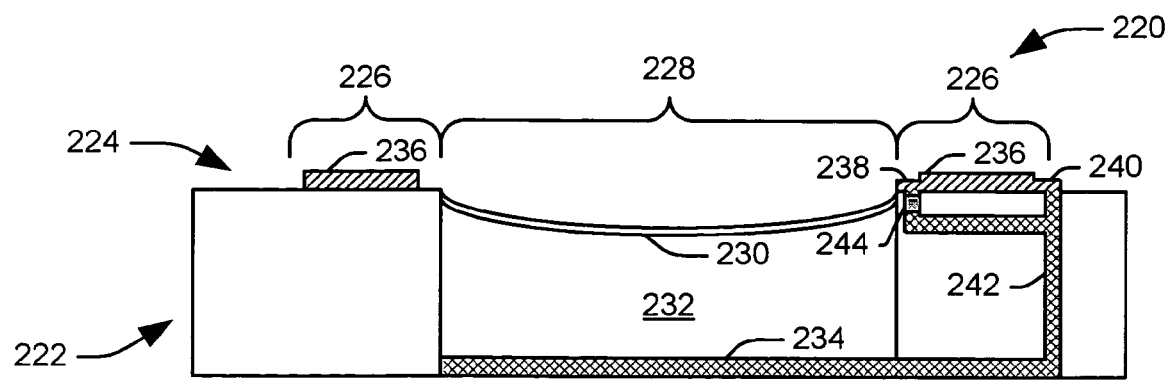
FIG. 5 illustrates an exemplary in vivo sensor in accordance with an aspect of the present invention.

FIG. 5 illustrates an exemplary in vivo sensor 220 in accordance with an aspect of the present invention. The illustrated in vivo sensor 220 is a pressure sensor, but the specific application and purpose of the sensor can vary in accordance with the present invention. The sensor includes a substrate 222 that can be comprised of a silicon material, but it will be appreciated that other materials may be used. The substrate 222 includes a contact surface 224 for making contact with a medium to be measured. For example, the contact surface 224 can be exposed to blood within an aneurysm sac or to aqueous humor within an eye.

The surface 224 includes an outer non-compliant region 226 and an inner compliant region 228 that can be fabricated, for example, using MEMS techniques, as an impedance element, the impedance of which varies as the inner compliant region 228 changes shape. The compliant region 228 comprises a diaphragm 230 as one plate of a capacitive element that is separated by a dielectric 232 from another plate 234 of the capacitive element. As the pressure of the medium increases, the diaphragm plate 230 flexes closer to the other non-compliant plate 234 to change the capacitance of the capacitive element in proportion to the pressure exerted on the diaphragm plate 230. In the illustrated embodiment, the dielectric comprises air, but other suitably compliant dielectrics such as hydrogel and silicone or various high dielectric oils, for example, may also be used, without deviating from the principles of the present invention.

An inductor coil 236, having respective first and second terminals 238 and 240 can be fabricated as part of the substrate 202. The inductor coil 236 is electrically coupled to the compliant region 228 (e.g., at the diaphragm 230) at its first terminal 238 and to the non-compliant plate 234 at a second terminal 240 via a conductive path 242 as to form a resonance or tank circuit. The inductor coil 236 is responsive to an external signal for energizing the sensor 220 so that the pressure may be determined. In the present embodiment, the inductor coil 236 is formed by disposing conductive material in a predetermined pattern, like a concentric spiraled pattern, for example, in the non-compliant region 226. It should be understood that the inductor region need not be embodied solely at the non-compliant region 226 and may be embodied as part of the compliant region 228 as well without deviating from the principles of the present invention.

In accordance with an aspect of the present invention, the resonant circuit comprising the inductor coil 236 and the capacitive element formed by the plates 230 and 234 may be excited into resonance by an external electromagnetic signal in the radio frequency (RF) range. Tank circuits of this type have a natural resonant frequency $f_o$ that, to the first order, depends of the values of the inductor and the capacitor as follows:

$$f_o = 1/2\pi(LC)^{1/2}$$

where L is the inductance and C is the capacitance.

Accordingly, as the capacitance of the sensor 220 changes, the resonant frequency $f_o$ of the tank circuit will change in proportion thereto.

In accordance with an aspect of the present invention, the first terminal 238 of the inductor coil 236 can be connected to the second terminal 240 of the inductor coil 236 through a nonlinear element 242. For example, the nonlinear element 242 can comprise a Schottky diode. This connection changes the response of the sensor 220, such that the sensor resonates at its natural resonant frequency, but produces a response signal having frequency components that differ from its natural resonant frequency. For example, the sensor 220 can act as a mixer to produce sum and difference frequencies from an excitation signal containing multiple frequency components. Accordingly, the response signal provided by the sensor 220 can be separated in frequency from the excitation signal to reduce interference between the signals.

In accordance with an aspect of the present invention, a high power excitation signal can be utilized to drive the resonance of the sensor 220 sufficiently high to produce a change in an electrical characteristic of the nonlinear element 242, such that the response of the sensor at the sum and different components is significantly attenuated when the excitation signal has a frequency equal to the resonant frequency of the sensor. For example, where the nonlinear element 242 is a diode, the circuit can be configured such that when the excitation signal reaches a resonance frequency, the voltage over the diode is sufficient to force the diode into forward bias, such that the electrical resistance of the diode is sharply reduced at the resonant frequency of the sensor 220, shorting the coil. In essence, the circuit is detuned when excitation frequency reaches the resonant frequency, such that the signal is greatly reduced or disappears.

Figure 6:
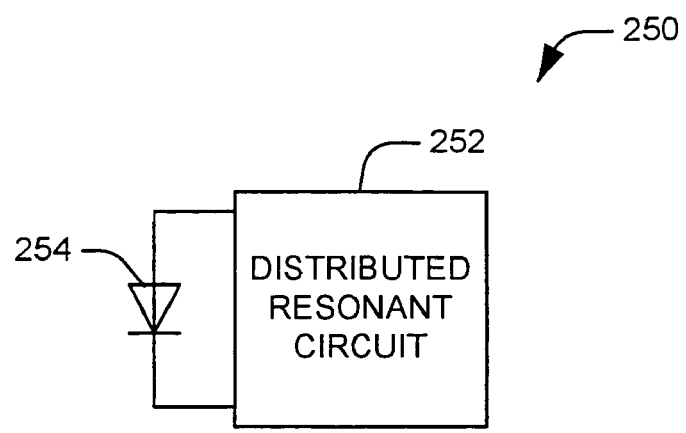
FIG. 6 illustrates a functional diagram of an exemplary in vivo sensor in accordance with an aspect of the present invention.

FIG. 6 illustrates a functional diagram of an exemplary in vivo sensor 250 in accordance with an aspect of the present invention. The sensor includes a distributed resonant circuit 252. For example, the distributed resonant circuit 252 can comprise an LC tank circuit. At least one diode 254 is operatively connected to the distributed resonant circuit. In accordance with an aspect of the present invention, the diode or diodes 254 can operate as a nonlinear element in the distributed resonant circuit 252, such that a response of the resonant circuit to an excitation signal will differ in frequency from the frequency of the excitation signal. For example, where a single excitation signal is used, the response signal can have a frequency twice that of the excitation frequency. Alternatively, where multiple excitation frequencies are utilized, the sensor can produce a response signal comprising respective sum and difference frequencies of the multiple excitation frequencies.

In addition, the circuit can be configured such that when the excitation signal reaches a resonance frequency, the voltage within the resonant circuit 252 is sufficient to force one or more of the at least one diode 254 into forward bias, shorting the resonant circuit 252. In essence, the circuit is detuned when excitation frequency reaches the resonant frequency, such that the response signal disappears. By monitoring the response signal for the detuning of the circuit, the resonant frequency of the sensor can be determined.

Figure 7:
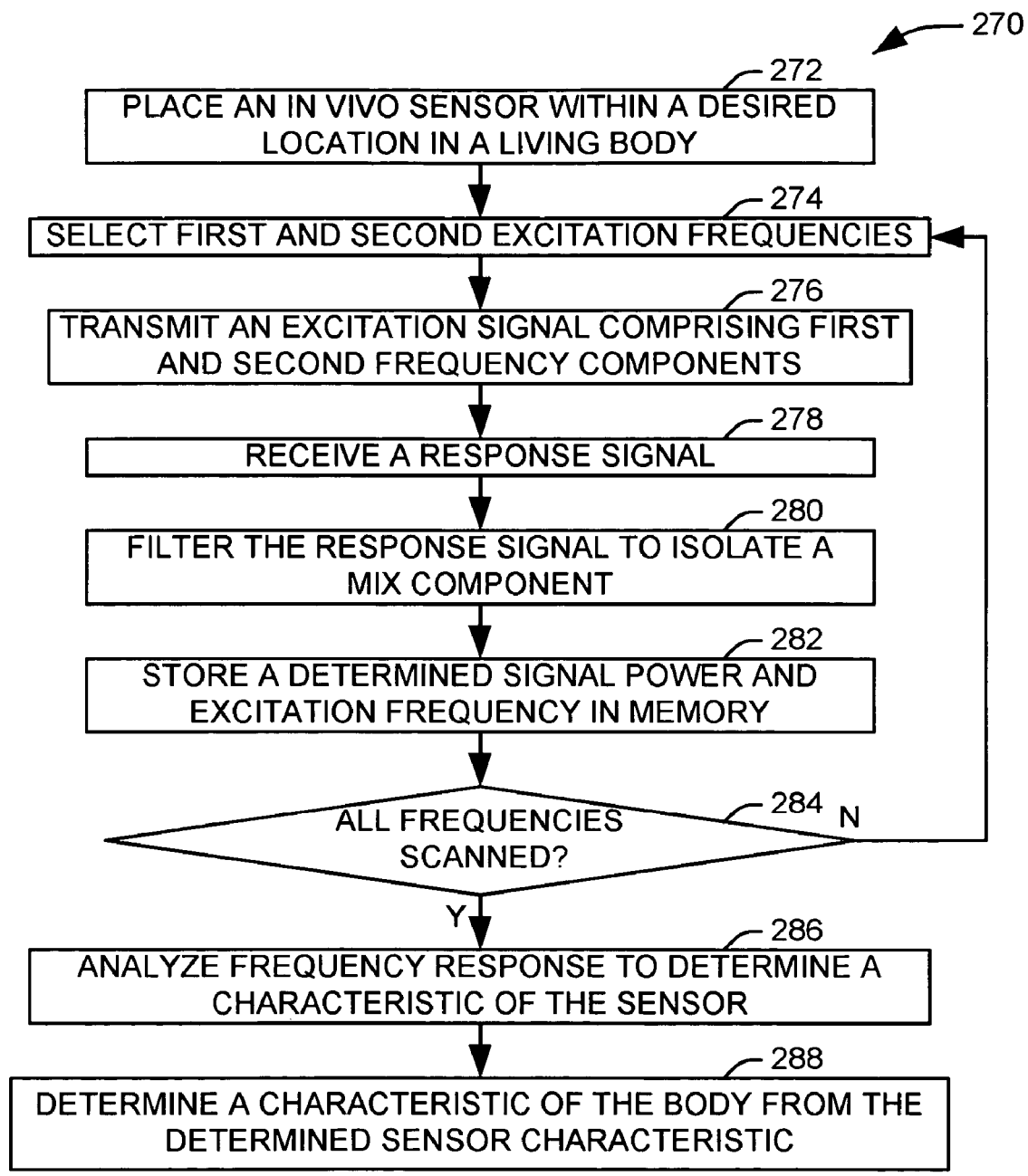
FIG. 7 illustrates an exemplary methodology for determining a characteristic within a living body in accordance with an aspect of the present invention.

FIG. 7 illustrates an exemplary methodology 270 for determining a characteristic of an in vivo sensor in accordance with an aspect of the present invention. At step 272, the in vivo sensor is implanted at a desired location within a living body. For example, the sensor can be implanted within an aneurysm sac, in the aqueous humor of a human eye, inside of a hydrocephalic shunt, within an artificial joint, or along the surface of an orthopedic implant. At step 274, first and second excitation frequencies can be selected from a frequency range of interest. For example, a minimum frequency within a frequency range of interest can be selected as the first excitation frequency in a first iteration and the first excitation signal can be advanced through the range of interest by a predetermined sweep increment in each successive iteration until a maximum frequency associated with the range of interest is achieved. A second excitation frequency can be determined at each iteration, for example, by adding a fixed offset value to the first excitation frequency to maintain a constant difference between the frequencies, sweeping the second excitation frequency in the opposite direction of the first excitation frequency as to maintain a constant sum of the frequencies, or referencing a constant, default value for the second frequency.

At step 276, a transmit signal is produced, comprising first and second frequency components having associated frequencies equal to the first excitation frequency and the second excitation frequency, respectively. The excitation signal induces a response signal at the in vivo sensor, with the response signal having frequency components corresponding to the sum and difference of the first and second excitation frequencies. It will be appreciated that the magnitude of the response signal will approach a maximum value when the associated frequencies of the excitation signal approach a resonant frequency of the sensor. At other excitation frequencies, the response signal will remain at an associated noise floor.

The response signal is received at the receive element at step 278. The response signal can be filtered at step 280 to isolate a mix component of the response signal, having a frequency equal to either the sum or difference of the excitation frequencies. At step 282, the power of the mix component and the pair of excitation frequencies that induced the signal are stored in memory as part of a frequency response. At step 284, it is determined if all desired frequencies within the frequency range of interest have been scanned. If not all of the frequencies have been scanned (N), the methodology returns to step 274 to select new excitation frequencies. If the termination event has occurred (Y), the methodology advances to step 286, At step 286, a desired characteristic of the sensor is determined from the frequency response. For example, an excitation frequency associated with a maximum power can be selected as the resonant frequency of the sensor and an impedance or capacitance associated with the sensor can be determined. Alternatively, a peak width measure associated with the frequency can be utilized to calculate a quality factor associated with the sensor. Once the desired characteristic has been determined, a characteristic of the body can be determined from the determined sensor characteristic at step 288. The methodology then terminates.

Figure 8:
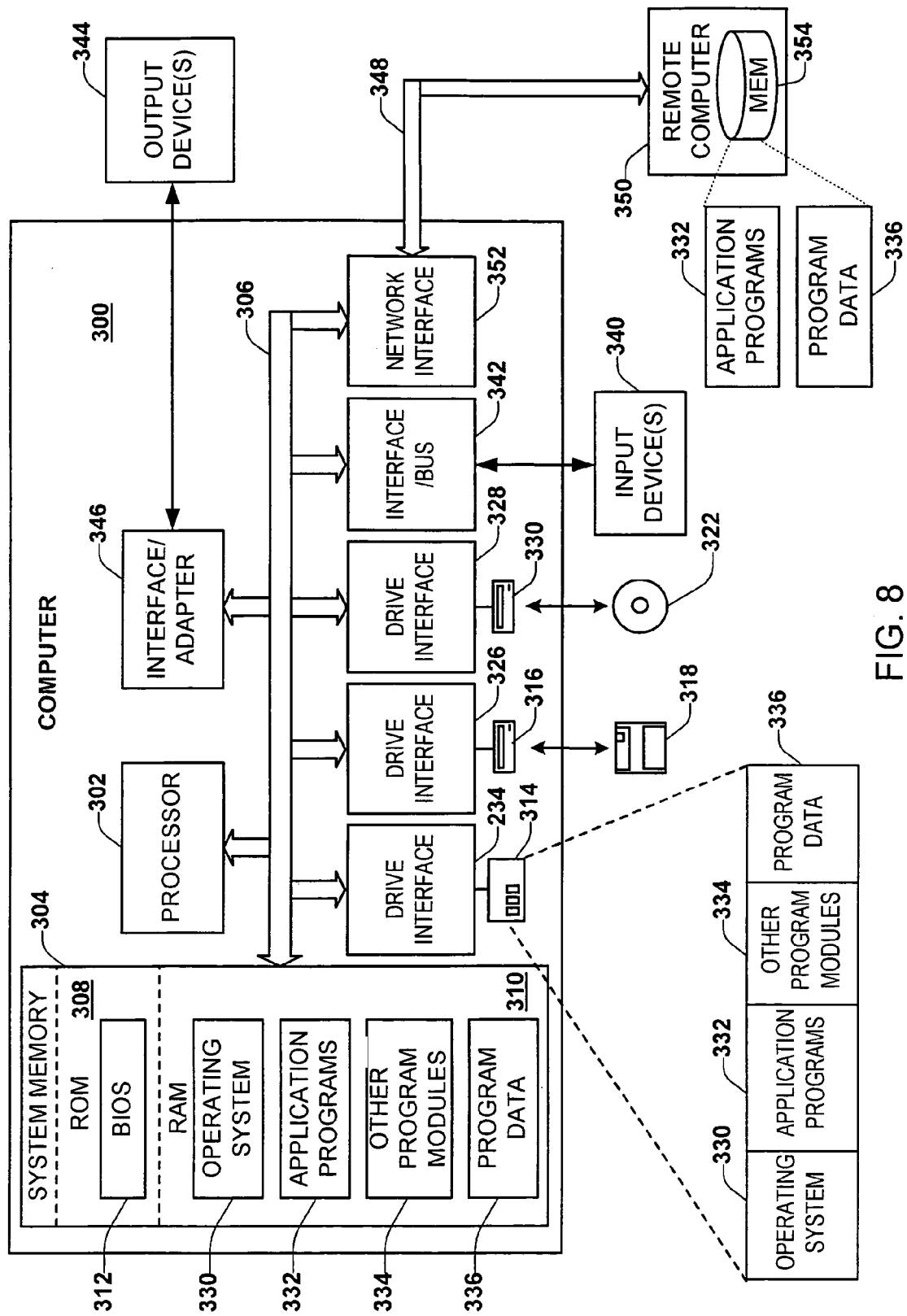
FIG. 8 illustrates a computer system that can be employed to implement systems and methods in accordance with an aspect of the present invention.

FIG. 8 illustrates a computer system 300 that can be employed to implement systems and methods described herein, such as based on computer executable instructions running on the computer system. Specifically, an RF probe in accordance with an aspect the present invention can be operatively connected to a computer system having some or all of the components herein described. The computer system 300 can be implemented on one or more general purpose networked computer systems, embedded computer systems, routers, switches, server devices, client devices, various intermediate devices/nodes and/or stand alone computer systems. Additionally, the computer system 300 can be implemented as part of the computer-aided engineering (CAE) tool running computer executable instructions to perform a method as described herein.

The computer system 300 includes a processor 302 and a system memory 304. A system bus 306 couples various system components, including the system memory 304 to the processor 302. Dual microprocessors and other multi-processor architectures can also be utilized as the processor 302. The system bus 306 can be implemented as any of several types of bus structures, including a memory bus or memory controller, a peripheral bus, and a local bus using any of a variety of bus architectures. The system memory 304 includes read only memory (ROM) 308 and random access memory (RAM) 310. A basic input/output system (BIOS) 312 can reside in the ROM 308, generally containing the basic routines that help to transfer information between elements within the computer system 300, such as a reset or power-up.

The computer system 300 can include a hard disk drive 314, a magnetic disk drive 316, e.g., to read from or write to a removable disk 318, and an optical disk drive 330, e.g., for reading a CD-ROM or DVD disk 322 or to read from or write to other optical media. The hard disk drive 314, magnetic disk drive 316, and optical disk drive 330 are connected to the system bus 306 by a hard disk drive interface 234, a magnetic disk drive interface 326, and an optical drive interface 328, respectively. The drives and their associated computer-readable media provide nonvolatile storage of data, data structures, and computer-executable instructions for the computer system 300. Although the description of computer-readable media above refers to a hard disk, a removable magnetic disk and a CD, other types of media which are readable by a computer, may also be used. For example, computer executable instructions for implementing systems and methods described herein may also be stored in magnetic cassettes, flash memory cards, digital video disks and the like.

A number of program modules may also be stored in one or more of the drives as well as in the RAM 310, including an operating system 330, one or more application programs 332, other program modules 334, and program data 336.

A user may enter commands and information into the computer system 300 through user input device 340, such as a keyboard, a pointing device (e.g., a mouse). Other input devices may include a microphone, a joystick, a game pad, a scanner, a touch screen, or the like. These and other input devices are often connected to the processor 302 through a corresponding interface or bus 342 that is coupled to the system bus 306. Such input devices can alternatively be connected to the system bus 306 by other interfaces, such as a parallel port, a serial port or a universal serial bus (USB). One or more output device(s) 344, such as a visual display device or printer, can also be connected to the system bus 306 via an interface or adapter 346.

The computer system 300 may operate in a networked environment using logical connections 348 to one or more remote computers 350. The remote computer 348 may be a workstation, a computer system, a router, a peer device or other common network node, and typically includes many or all of the elements described relative to the computer system 300. The logical connections 348 can include a local area network (LAN) and a wide area network (WAN).

When used in a LAN networking environment, the computer system 300 can be connected to a local network through a network interface 352. When used in a WAN networking environment, the computer system 300 can include a modem (not shown), or can be connected to a communications server via a LAN. In a networked environment, application programs 332 and program data 336 depicted relative to the computer system 300, or portions thereof, may be stored in memory 354 of the remote computer 350.

From the above description of the invention, those skilled in the art will perceive improvements, changes, and modifications. Such improvements, changes, and modifications within the skill of the art are intended to be covered by the appended claims.

Having described the invention, we claim:

1. A method for in vivo sensing, comprising the steps of:
   producing an excitation signal, having a first frequency component and a second frequency component, wherein a first excitation frequency associated with the first frequency component is swept through a plurality of excitation frequencies within a frequency range of interest;
   receiving a response signal from an in vivo sensor, the response signal comprising a mix component having a frequency equal to one of a sum of a first excitation frequency associated with the first frequency component and a second excitation frequency associated with the second frequency component and a difference between the first and second excitation frequencies; and
   evaluating the mix component to determine a characteristic of the in vivo sensor.

2. The method of claim 1, wherein the step of evaluating the mix component comprises the step of determining a frequency associated with a maximum amplitude of the mix component.

3. The method of claim 2, wherein the step of evaluating the mix component further comprises the step of calculating an associated capacitance of the in vivo sensor.

4. The method of claim 2, wherein the step of evaluating the mix component further comprises the step of calculating an associated impedance of the in vivo sensor.

5. The method of claim 1, wherein the step of evaluating the mix component further comprises the step of determining a peak width associated with the mix component.

6. The method of claim 5, wherein the step of evaluating the mix component further comprises the step of calculating an associated quality factor of the in vivo sensor.

7. The method of claim 1, further comprising maintaining the second excitation frequency at a fixed offset from the first excitation frequency, such that the difference between the first and second excitation frequencies is constant.

8. The method of claim 1, wherein producing an excitation signal comprises producing an excitation signal of sufficient power to change an electrical characteristic of a nonlinear element associated with the in vivo sensor.

9. The method of claim 8, evaluating the mix component comprises determining a value for the first excitation frequency at which the electrical characteristic of the nonlinear element is changed.

10. The method of claim 8, wherein the nonlinear element is a diode and the change in the electrical characteristic comprises a decrease in electrical resistance due to a forward bias voltage across the diode.

11. A computer program product, encoded on a computer readable medium and operative in a data processing system, for controlling an RF probe, comprising:
    a frequency selector that selects a first excitation frequency and a second excitation frequency for the probe;
    an amplitude detector that, for each of a plurality of selected values for the first excitation frequency, determines an associated power of a mix component, having an associated frequency equal to one of a sum of the first and second excitation frequencies and a difference between the first and second excitation frequencies, of a response signal from an in vivo sensor to record a frequency response for the signal; and
    a response analyzer that evaluates the recorded frequency response to determine a characteristic of the in vivo sensor.

12. The computer program product of claim 11, wherein the frequency selector selects the first and second excitation frequencies such that their sum remains constant.

13. The computer program product of claim 11, wherein the frequency selector selects the first and second excitation frequencies such that the difference between the first and second excitation frequencies remains constant.

14. An RF probe assembly for determining a characteristic of an in vivo sensor having an associated nonlinear element, comprising:
    a transmit element that provides an excitation signal for the probe, the excitation signal comprising a first frequency component, having a first associated frequency, and a second frequency component, having a second associated frequency;
    a response element that receives a response signal from the in vivo sensor, the response signal comprising a mix component having a frequency equal to one of a sum of the first and second frequencies and a difference between the first and second frequencies; and
    a system control that evaluates the mix component to determine the characteristic of the associated in vivo sensor.

15. The RF probe assembly of claim 14, wherein the first and second frequencies are maintained at a constant difference in frequency and the assembly further comprises a bandpass filter operative to isolate the mix component and a lock-in amplifier that amplifies the mix component.

16. The RF probe assembly of claim 14, the system control comprising an arbitrary waveform generator that controls the transmit element as to provide the excitation element and a network analyzer that evaluates the mix component.

17. The RF probe assembly of claim 14, the in vivo sensor comprising a pressure sensor and the determined characteristic of the in vivo sensor comprising the impedance.

18. The RF probe assembly of claim 14, the transmit and response element comprising a pair of orthogonal coils.

19. The RF probe assembly of claim 14, the transmit element being operative to produce a excitation signal of sufficient power to induce a voltage within the in vivo sensor large enough to alter an electrical property of the nonlinear element when the first excitation frequency has a value equal to the value of a resonant frequency associated with the in vivo sensor.

20. The RF probe assembly of claim 19, wherein the nonlinear element is a diode, and the induced voltage drives the diode into forward bias, such that the electrical resistance of the diode is sharply reduced.

* * * * *